(12) United States Patent
Christensen, IV et al.

(10) Patent No.: US 6,172,118 B1
(45) Date of Patent: Jan. 9, 2001

(54) COMPOUNDS

(75) Inventors: Siegfried B. Christensen, IV, Philadelphia, PA (US); Cornelia J. Forster, Pelham, NH (US)

(73) Assignee: SmithKline Beecham Corporation, Philadelphia, PA (US)

( * ) Notice: Under 35 U.S.C. 154(b), the term of this patent shall be extended for 0 days.

(21) Appl. No.: 09/291,592

(22) Filed: Apr. 8, 1999

Related U.S. Application Data

(60) Provisional application No. 60/081,643, filed on Apr. 14, 1998.

(51) Int. Cl.[7] .................................................... A61K 31/12
(52) U.S. Cl. .......................... 514/684; 514/256; 514/683; 544/297; 568/329; 568/330
(58) Field of Search ..................................... 568/308, 329, 568/330; 514/256, 683, 684; 544/297

(56) References Cited

PUBLICATIONS

Honda, et al., "Chiral synthesis of phosphodiesterase inhibitor, ®–(–)–rolipra, by means of enantioselective deprotonation strategy". Heterocycles, Jan. 1996, vol. 42, No. 1, pp. 109–111, especialy p. 10.

*Primary Examiner*—Amelia Owens
(74) *Attorney, Agent, or Firm*—James M. Kanagy; Charles M. Kanagy

(57) ABSTRACT

This invention relates to ketones, alcohols and amines represented by the likes of of 3-(3-cyclopentyloxy-4-methoxyphenyl)-3-phenylethynylcyclobutan-1-one. They are useful as PDE 4 antagonists.

10 Claims, No Drawings

COMPOUNDS

This application claims priority from provisional application Ser. No. 60/081,643 filed Apr. 14, 1998.

SCOPE OF THE INVENTION

This invention covers certain ketones and amines represented by the likes of 3-(3-cyclopentyloxy-4-methoxyphenyl)-3-phenylethynylcyclobutan-1-one. These ketones are selective for inhibiting the catalytic site in the phosphodiesterase isoenzyme denominated 4 (PDE 4 hereafter) while exhibiting little or no affinity for a second binding site on the PDE 4 isoenzyme denominated the high affinity rolipram binding site. A method for treating diseases related to inhibiting the catalytic site in the PDE 4 isoenzyme, e.g., asthma, COPD, etc. is also disclosed.

AREA OF THE INVENTION

Cyclic nulceotide phosphodiesterases (PDEs) represent a family of enzymes that hydrolyze the ubiquitous intracellular second messengers, adenosine 3',5'-monophosphate (cAMP) and guanosine 3',5'-monophosphate (cGMP) to their corresponding inactive 5'-monophosphate metabolites. At least five distinct PDE isoenzymes are believed to exist, each possessing unique physical and kinetic charactersitics and each representing a product of a different gene family. Also the distribution of these isoenzymes appears to differ markedly among cell types.

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE 4, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE 4 inhibitors are markedly potentiated when adenylate cyclase activity of target cells is elevated by appropriate hormones or autocoids, as would be the case in vivo. Thus PDE 4 inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35,(10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

The novel compounds of this invention are represented by Formula (I):

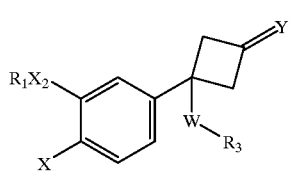

(I)

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be unsubstituted or substituted with one or more fluorines;

m is 0 to 2;

n is 1 to 4;

r is 0 to 6;

$R_4$ and $R_5$ are independently hydrogen or C1-2 alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in —$(CR_4R_5)_nO(CR_4R_5)_mR_6$;

X is $VR_2$, halogen, nitro, $NR_4R_5$, or formyl amine;

V is O or $S(O)_{m'}$;

m' is 0, 1, or 2;

$X_2$ is O or $NR_8$;

$R_2$ is —$CH_3$ or —$CH_2CH_3$ unsubstituted or substituted by 1 or more fluorines;

$R_3$ is $COOR_{14}$, $C(O)NR_4R_{14}$ or $R_7$;

W is alkyl of 2 to 6 carbon atoms, alkenyl of 2 to 6 carbon atoms or alkynyl of 2 to 6 carbon atoms;

Z is O, $NR_9$, $NOR_8$, NCN, C(—CN)$_2$, $CR_8CN$, $CR_8NO_2$, $CR_8C(O)OR_8$, $CR_8C(O)NR_8R_8$, C(—CN)NO$_2$, C(—CN)C(O)OR$_9$, C(—CN)C(O)NR$_8R_8$;

Y is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$, or =Y is 2-(1,3-dithiane), 2-(1,3-dithiolane), dimethylthio ketal, diethylthio ketal, 2-(1,3-dioxolane), 2(1,3-dioxane), 2-(1,3-oxathiolane), dimethyl ketal or diethyl ketal;

$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —NO$_2$, —NR$_{10}R_{11}$, —C(O)R$_8$, —CO$_2R_8$, —O(CH$_2$)$_qR_8$, —CN, —C(O)NR$_{10}R_{11}$, —O(CH$_2$)$_qC(O)NR_{10}R_{11}$, —O(CH$_2$)$_qC(O)R_8$, —NR$_{10}$C(O)NR$_{10}R_{11}$, —NR$_{10}$C(O)R$_{11}$, —NR$_{10}$C(O)OR$_9$, —NR$_{10}$C(O)R$_{13}$, —C(NR$_{10}$)NR$_{10}R_{11}$, —C(NCN)NR$_{10}R_{11}$, —C(NCN)SR$_9$, —NR$_{10}$C(NCN)SR$_9$, —NR$_{10}$C(NCN)NR$_{10}R_{11}$, —NR$_{10}$S(O)$_2R_9$, —S(O)$_{m'}R_9$, —NR$_{10}$C(O)C(O)NR$_{10}R_{11}$, —NR$_{10}$C(O)C(O)R$_{10}$, or $R_{13}$;

q is 0, 1, or 2;

$R_{12}$ is $R_{13}$, $C_3$–$C_7$ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;

$R_8$ is hydrogen or $R_9$;

$R_{8'}$ is $R_8$ or fluorine;

$R_9$ is $C_{1-4}$ alkyl unsubstituted or substituted by one to three fluorines;

$R_{10}$ is $OR_8$ or $R_{11}$;

$R_{11}$ is hydrogen, or $C_{14}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_8$ and $R_{14}$ are as $NR_8R_{14}$ they may together with the nitrogen form a 5 to 7 membered ring comprised only of carbon atoms or carbon atoms and at least one heteroatom selected from O, N, or S; provided that:

$R_{15}$ is $C(O)R_{14}$, $C(O)NR_4R_{14}$, $S(O)_2R_7$, or $S(O)_2NR_4R_{14}$;

or a pharmaceutically acceptable salt thereof.

A second set of compounds of this invention are represented by Formula (II)

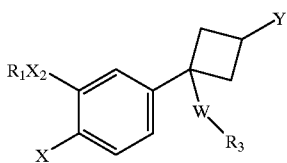

(II)

wherein the several groups are the same as those of formula (I) except:

Y is —(CR$_4$R$_5$)$_q$Z';

Z' is OR$_{14}$, OR$_{15}$, SR$_{14}$, S(O)$_m$R$_7$, S(O)$_2$NR$_{10}$R$_{14}$, NR$_{10}$R$_{14}$, NR$_{14}$C(O)R$_9$, NR$_{10}$C(Y'R$_{14}$, NR$_{10}$C(O)OR$_7$, NR$_{10}$C(Y')NR$_{10}$R$_{14}$, NR$_{10}$S(O)$_2$NR$_{10}$R$_{14}$, NR$_{10}$C(NCN) NR$_{10}$R$_{14}$, NR$_{10}$S(O)$_2$R$_7$, NR$_{10}$C(CR$_4$NO$_2$)NR$_{10}$R$_{14}$, NR$_{10}$C (NCN)SR$_9$, NR$_{10}$C(CR$_4$NO$_2$)SR$_9$, NR$_{10}$C(NR$_{10}$)NR$_{10}$R$_{14}$, NR$_{10}$C(O)C(O)NR$_{10}$R$_{14}$, or NR$_{10}$C(O)C(O)OR$_{14}$;

Y' is O or S;

(g) When R$_{12}$ is N-pyrazolyl,, N-imidazolyl, N-triazolyl, N-pyrrolyl, N-piperazinyl, or N-morpholinyl, then q is not 1; or a pharmaceutically acceptable salt thereof.

This invention also relates to the pharmaceutical compositions comprising a compound of Formula (I) and (II) and a pharmaceutically acceptable carrier or diluent.

The invention also relates to a method of mediation or inhibition of the enzymatic activity (or catalytic activity) of PDE 4 in mammals, including humans, which comprises administering to a mammal in need thereof an effective amount of a compound of Formula (I) and (II) as shown below.

The invention further provides a method for the treatment of allergic and inflammatory disease which comprises administering to a mammal, including humans, in need thereof, an effective amount of a compound of Formula (I) and (II).

The invention also provides a method for the treatment of asthma which comprises administering to a mammal, including humans, in need thereof, an effective amount of a compound of Formula (I) and (II).

This invention also relates to a method of inhibiting TNF production in a mammal, including humans, which method comprises administering to a mammal in need of such treatment, an effective TNF inhibiting amount of a compound of Formula (I) and (II). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I) and (II).

Compounds of Formula (I) and (II) are also useful in the treatment of additional viral infections, where such viruses are sensitive to upregulation by TNF or will elicit TNF production in vivo.

In addition, compounds of Formula (I) and (II) are also useful in treating yeast and fungal infections, where such yeast and fungi are sensitive to upregulation by TNF or will elicit TNF production in vivo.

DETAILED DESCRIPTION OF THE INVENTION

Phosphodiesterase 4 inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE 4 inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I) and (II). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (I) and (II).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (HIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) and (II) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The compounds of Formula (I) and (II) may also be used for inhibiting and/or reducing the toxicity of an anti-fungal, anti-bacterial or anti-viral agent by administering an effective amount of a compound of Formula (I) and (II) to a mammal in need of such treatment. Preferably, a compound of Formula (I) and (II) is administered for inhibiting or reducing the toxicity of the Amphotericin class of compounds, in particular Amphotericin B.

The term "C$_{1-3}$ alkyl", "C$_{1-4}$ alkyl", "C$_{1-6}$ alkyl" or "alkyl" groups as used herein is meant to include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

"Alkenyl" means both straight or branched chain radicals of 1 to 6 carbon lengths, unless the chain length is limited thereto, including but not limited to vinyl, 1-propenyl, 2-propenyl, or 3-methyl-2-propenyl.

The term "cycloalkyl" or "cycloalkyl alkyl" means groups of 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain is meant to include both straight or branched chain radicals of 1 to 4 carbon atoms. "Heteroaryl" means an aromatic ring system containing one or more heteroatoms.

"Halo" means all halogens, i.e., chloro, fluoro, bromo, or iodo.

"Inhibiting the production of IL-1" or "inhibiting the production of TNF" means:

a) a decrease of excessive in vivo L-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferrably, his cytokine is TNF-α.

All of the compounds of Formula (I) and (II) are useful in the method of inhibiting the production of TNF, preferably by macrophages, monocytes or macrophages and monocytes, in a mammal, including humans, in need thereof. All of the compounds of Formula (I) and (II) are useful in the method of inhibiting or mediating the enzymatic or catalytic activity of PDE 4 and in treatment of disease states mediated thereby.

Preferred compounds are as follows:

When $R_1$ for the compounds of Formula (I) and (II) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) and (II) are $CH_2$-cyclopropyl, $CH_2$-$C_{5-6}$ cycloalkyl, $C_{4-6}$ cycloalkyl unsubstituted or substituted with OH, $C_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term is $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH(-CH_3)$—, for instance. The individual hydrogen atoms of the repeating methylene unit or the branching hydrocarbon can be unsubstituted or be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published Nov. 5, 1987, whose disclosure is incorporated herein by reference in its entirety.

Preferred Z terms are O, NCN, $NR_7$, $NOR_{14}$, $NOR_{15}$, $NNR_4R_{14}$, $NNR_4R_{15}$, 2-(1,3-dithiane), dimethylthio ketal, 2-(1,3-dioxolane), or dimethyl ketal. More preferred are O, $NR_7$, $NOR_{14}$, $NOR_{15}$, and 2-(1,3-dioxolane).

Preferred X groups for Formula (I) and (II) are those wherein X is $YR_2$ and Y is oxygen. The preferred $X_2$ group for Formula (I) and (II) is that wherein $X_2$ is oxygen. The preferred $X_3$ group for Formula (I) and (II) is that wherein X3 is hydrogen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_7$ moieties include $R_{13}$, unsubstituted or substituted —$(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl), $(CH_2)_{1-2}$(2-thienyl), $(CH_2)_{1-2}$(4-thiazolyl), unsubstituted or substituted pyrimidinyl, and substituted or unsubstituted $(CH_2)_{0-2}$phenyl.

Preferred rings when $R_{10}$ and $R_{11}$ in the moiety —$NR_{10}R_{11}$ together with the nitrogen to which they are attached form a 5 to 7 membered ring comprised only of carbon atoms or carbon atoms and at least one heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl ring.

Preferred rings when $R_8$ and $R_{14}$ in the moiety —$NR_8R_{14}$ together with the nitrogen to which they are attached may form a 5 to 7 membered ring comprised only of carbon atoms or carbon atoms and at least one heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I) and (II). Illustrations of such carbon substitutions includes, but is not limited to, 2-($R_7$)-1-imidazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_8R_{14}$ which contain a heterocyclic ring are 5-($R_{14}$)-1-tetrazolyl, 2-($R_{14}$)-1-imidazolyl, 5-($R_{14}$)-2-tetrazolyl, 4-($R_{14}$)-1-piperazinyl, or 4-($R_{15}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (S-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, 5-oxazolidinyl), (2-, 4-, or 5-thiazolidinyl), or (2-, 4-, or 5-imidazolidinyl).

When the $R_7$ group is unsubstituted or substituted by a heterocyclic ring such as imidazolyl, pyrazolyl, pyrimidinyl, triazolyl, tetrazolyl, or thiazolyl, the heterocyclic ring itself may be unsubstituted or substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

W is preferably alkyl, alkenyl or alkynyl of 3 to 5 carbon atoms, and where it is alkenyl or alkynyl, that one or two double or triple bonds be present. It is most preferred that W is ethynyl or 1,3-butadiynyl.

Preferred are those compounds of Formula (I) and (II) wherein $R_1$ is —$CH_2$— cyclopropyl, —$CH_2$-$C_{5-6}$ cycloalkyl, —$C_{4-6}$ cycloalkyl unsubstituted or substituted with OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}$ OH; $R_2$ is methyl or fluoro-substituted alkyl, R, is R, where R, is an unsubstituted or substituted aryl or heteroaryl ring, X is $YR_2$, and Z is O, $NR_7$.

Most preferred are those compounds of Formula (I) are those wherein $R_1$ is —$CH_2$-cyclopropyl, cyclopentyl, 3-hydroxycyclopentyl, methyl or $CF_2H$; X is $VR_2$; V is oxygen; $X_2$ is oxygen; $R_2$ is $CF_2H$ or methyl, W is ethynyl or 1,3-butadiynyl, $R_3$ is a substituted or unsubstituted pyrimidinyl ring, and Z is O or $NR_7$.

As regards preferred compounds of Formula (II) they are the same as for those of Formula (I) where Formula (II) shares a group in common with Formula (I). As regards the Y group in Formula (II), the preferred embodiment is where $R_4$ and $R_5$ are hydrogen, q is 0 or 1 and Z' is $OR_{14}$, $OR_{15}$, or $NR_{10}R_{14}$, most particularly $NR_{10}R_{14}$.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid. If the parent compound is an acid, it is treated with an inorganic or organic base dissolved in a suitable solvent.

Pharmaceutical compositions of the present invention comprise a pharmaceutical carrier or diluent and some amount of a compound of the Formula (I) and (II). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

It will be recognized that some of the compounds of Formula (I) and (II) may exist in both racemic and optically active forms; some may also exist in distinct diastereomeric forms possessing distinct physical and biological properties. All of these compounds are considered to be within the scope of the present invention.

The following examples are given to further illustrate the described invention. These examples are intented solely for illustrating the invention and should not be read to limit the invention in any manner. Reference is made to the claims for what is reserved to the inventors hereunder.

No unacceptable toxicological effects are expected when these compounds are administered in accordance with the present invention.

METHODS OF PREPARATION

Synthetic Scheme(s) With Textual Description

Cyanocyclobutanone 1-Scheme 1, prepared as described in an accompanying patent application filed on even date herewith may be protected, for example, as a ketal, by treatment with suitable reagents, such as bis (trimethylsilyloxy)ethane and catalytic trimethylsilyl trifluoromethanesulfonate, in a suitable solvent, such as dichloromethane. The nitrile may then be reduced by a suitable reagent, such as diisobutylaluminum hydride, in a suitable solvent, such as toluene or an ether, such as tetrahydrofuran and tetrabutyl methyl ether. Aldehyde 2-Scheme 1 may be homologated to the alkyne by treatment with an appropriate reagent, such as dialkyl diazomethylphosphonate, [Seyferth et al, *J. Org. Chem.,* 36: 1379, 1971 and a suitable base, such as potassium t-butoxide, in a suitable solvent, such as tetrahydrofuran. Deprotection of the ketal may be achieved by treatment with an acidic reagent, such as hydrogen chloride or p-toluenesulfonic acid, in an aqueous solvent, such as tetrahydrofuran, at temperatures from room temperature to reflux, preferably at 60° C. Terminal alkyne 3-Scheme 1 may be coupled with an aryl bromide or iodide, such as iodobenzene, using an appropriate catalyst system, such as tetrakis(triphenylphosphine)palladium(0) and copper(I) iodide, in a suitable solvent, such as triethylamine, at elevated temperature, preferably at 85° C., to provide the phenylethynylcyclobutanone 4 Scheme 1. [Brandsma et al, *Syn. Comm.,* 20: 1889, 1990].

Scheme 1

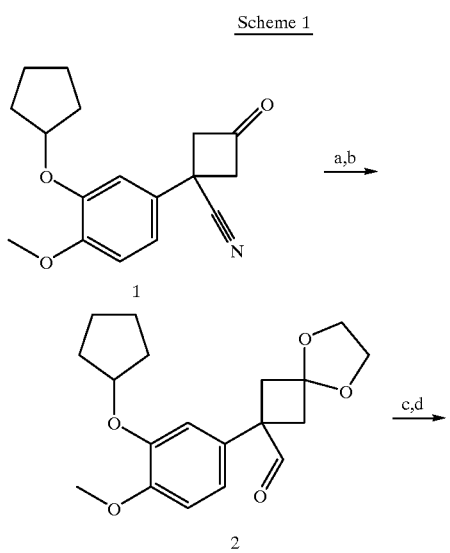

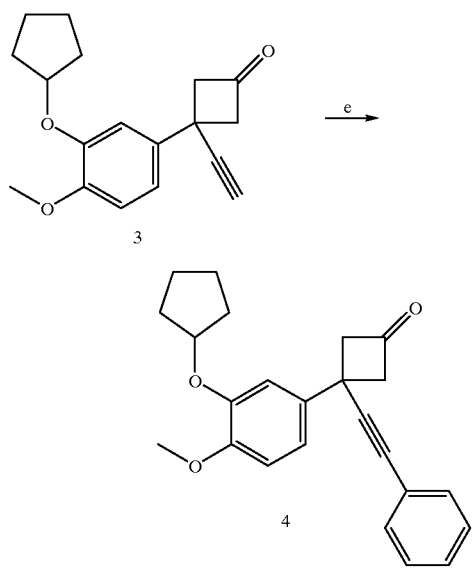

Reagents: a) TMSOCH$_2$CH$_2$OTMS, TMSOTf, CH$_2$Cl$_2$, -78° C. to RT;
b) DIBAL-H, THF, TBME;
c) N$_2$CHP(O)(OMe)$_2$, KO$^t$Bu, THF, -78° C. to RT;
d) HCl, H$_2$O, THF, 60° C.;
e) PhI, (PPh$_3$)$_4$Pd, CuI, Et$_3$N, 85° C.

Phenylethynylcyclobutanone 1 Scheme 2 may be treated with a suitable reagent, such as methoxymethyldiphenylphosphonium chloride, and a suitable base, such as phenyllithium, in a suitable solvent, such as ether or tetrahydrofuran. The resulting methyl vinyl ether 2-Scheme 2 may be hydrolyzed by treatment with an acidic reagent, such as p-toluenesulfonic acid, in a suitable aqueous solvent, such as isopropanol, at elevated temperature, preferably at reflux. [Demopoulos et al. *J. Het. Chem.,* 25: 635, 1988] Separation of cis and trans isomers may conveniently be carried out at this stage. Aldehyde 3a- or 3b-Scheme 2 may be transformed into the amine by, for example, reductive amination by treatment with suitable reagents, such as ammonium acetate and sodium cyanoborohydride, followed by hydrogen chloride, in a suitable solvent, such as methanol, to provide the aminomethylcyclobutane 4a- or 4b-Scheme 2

Scheme 2

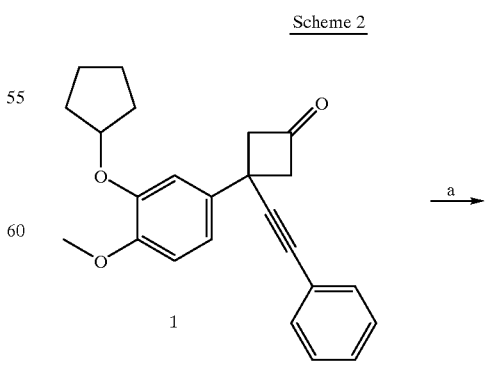

-continued

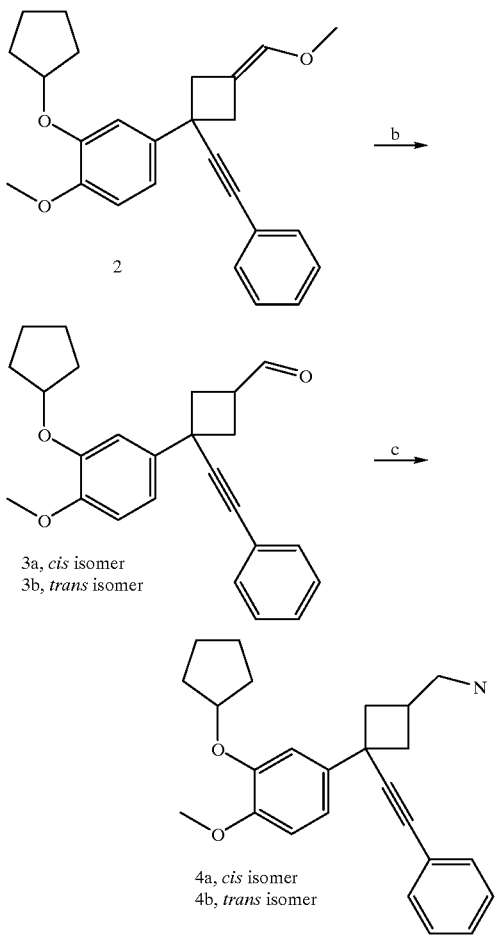

3a, *cis* isomer
3b, *trans* isomer

4a, *cis* isomer
4b, *trans* isomer

Reagents: a) CH$_3$OCH$_2$PPh$_3$$^+$Cl$^-$, PhLi, Et$_2$O, 0° C. to RT;
b) *p*TsOH, *i*PrOH, H$_2$O, reflux;
c) i. NH$_4$OAc, NaBH$_3$CN, MeOH, 4 A sieves; ii. HCl, MeOH.

Terminal alkyne 1-Scheme 3 may be reduced to the alcohol by a variety of reagents, such as a borohydride, especially lithium borohydride, in a suitable solvent, such as an alcohol, such as ethanol, or an ether, such as dimethoxyethane or tetrahydrofuran, at temperatures from −78° C. to room temperature. The mixture of cis and trans alcohols may then be subjected to Mitsunobu reaction conditions [Mitsunobu, *Synth*, 1, 1981], for example with diethyl azodicarboxylate, triphenylphosphine and phthalimide, in a suitable solvent, such as tetrahydrofuran, to give a mixture of phthalimidocyclobutanes, the cis and trans isomers of which may conveniently be separated.

Trans-phthalimidocyclobutane 2-Scheme 3 may be elaborated to the amine, for example with hydrazine, in a suitable solvent, such as ethanol and tetrahydrofuran, and protected, for example as the t-butylcarboxylate, by treatment with a suitable reagent, such as di-t-butyldicarbonate, in a suitable solvent, such as dichloromethane. Terminal alkyne 3-Scheme 3 may be coupled to an aryl bromide or iodide, such as iodobenzene, with an appropriate catalyst system, such as tetrakis(triphenylphosphine)palladium(0) and copper(I) iodide, in a suitable solvent, such as triethylamine, at elevated temperatures, preferably at 85° C. [Brandsma et al, *Syn. Comm.*, 20: 1889, 1990] The intermediate may be deprotected, for example with trifluoracetic acid, in a suitable solvent, such as dichloromethane, to give the trans-phenylethynylcyclobutylamine 4-Scheme 3.

Terminal alkyne 3-Scheme 3 may be reacted with even unreactive aryl iodides and bromides, such as 2-amino-5-iodopyrimidine, in the presence of a base, such as diethylamine, in a suitable solvent, such as dimethyl sulfoxide, using an appropriate catalyst system, such as tetrakis(triphenylphosphine)palladium(O) and copper(I) iodide, at elevated temperatures, preferably at 65° C. The intermediate may be deprotected, for example with trifluoracetic acid, in a suitable solvent, such as dichloromethane, to provide the trans-(2-aminopyrimidin-5-ylethynyl)cyclobutylamine 5-Scheme 3.

Scheme 3

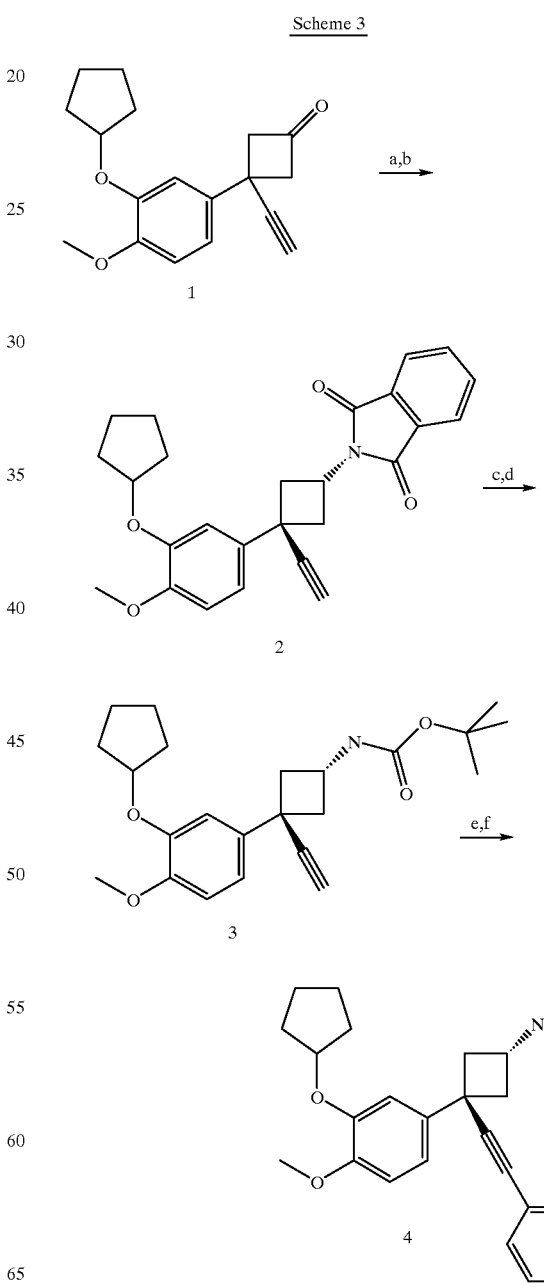

Scheme 4

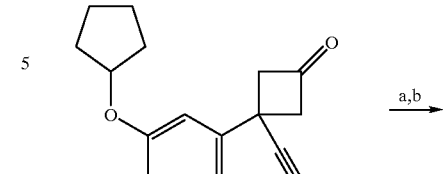

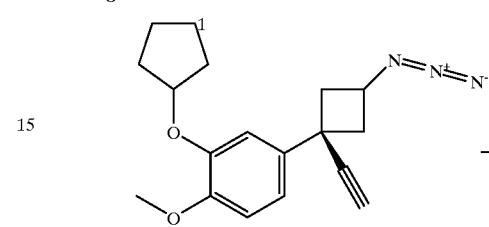

2a, *trans* isomer
2b, *cis* isomer

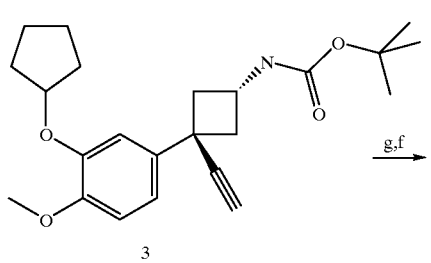

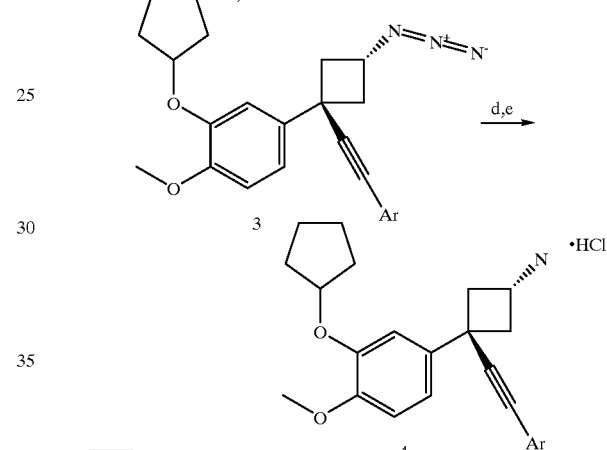

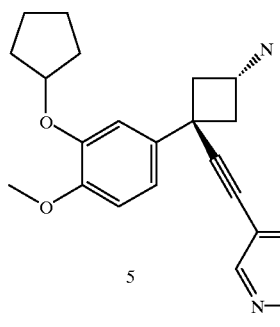

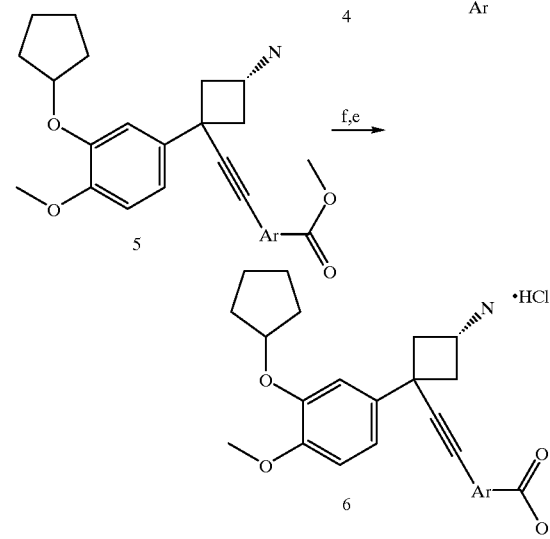

Reagents: a) LiBH₄, THF, -30° C.;
b) DEAD, PPh₃, phthalimide, THF;
c) N₂H₄•H₂O, THF, EtOH;
d) (*t*-BuO₂Cl₂)O, CH₂Cl₂;
e) PhI, (PPH₃)₄Pd, CuI, Et₃N, 85° C.;
f) TFA, CH₂Cl₂;
g) (PPh₃)₄Pd, CuI, 2-amino-5-iodopyrimidine, DMSO, Et₂NH, 65° C.

Reagents: a) LiBH₄, THF, -78° C.;
b) DEAD, Ph₂P(O)N₃, PPh₃, THF;
c) ArI, (PPh₃)₄Pd, CuI, Et₃N, 85° C.;
d) PPh₃, pyridine, NH₃, MeOH;
e) HCl, Et₂O;
f) KOH, THF, MeOH, H₂O.

Terminal alkyne 1-Scheme 4 may be subjected to Mitsunobu [Pearson et al, *J. Org. Chem.*, 54: 4235, 1989] reaction conditions, for example with diphenylphosphoryl azide, diethyl azodicarboxylate and triphenylphosphine, in a suitable solvent, such as tetrahydrofuran, resulting in a mixture of cis and trans azides 2a- and 2b-Scheme 4, which may conveniently be separated. Trans-azide 2a-Scheme 4 may be coupled with an aryl iodide or bromide using a suitable catalyst system, such as tetrakis(triphenylphosphine)palladium(0) and copper(I) iodide, in a suitable solvent, such as triethylamine, at elevated temperatures, preferably at 85° C. [Brandsma et al, *Syn. Comm.*, 20: 1889, 1990] Azide 3-Scheme 4 may be reduced with a suitable reducing system, such as triphenylphosphine, in the presence of a suitable base, such as pyridine, in a suitable solvent, such as ammoniacal methanol. Salt formation with, for example, ethereal hydrogen chloride, provides the amine salts 4-Scheme 4. In those cases where the coupled aryl group is a benzoate ester 5-Scheme 4, saponification may be achieved by a variety of reaction conditions, for example with potassium hydroxide in tetrahydrofuran, methanol and water. Salt formation with, for example, ethereal hydrogen chloride provides the amine salts 6-Scheme 4

SYNTHETIC EXAMPLES

Example 1

3-(3-Cyclopentyloxy-4-methoxyphenyl)-3-phenylethynylcyclobutan-1-one, 1a 3-(3-Cyclopentyloxy-4-methoxyphenyl)-3-ethynylcyclobutan-1-(1,3-dioxolane ketal). To a suspension of potassium tert-butoxide (1.40 g, 12.5 mmol) in tetrahydrofuran (50 mL) at −78° C. under an argon atmosphere was added via cannula a −78° C. solution of dimethyl diazomethylphosphonate (1.88 g, 12.5 mmol) (preparation described in PCT application PCT/US95/1671 1, published Jul. 4, 1996 as WO96/19988) in tetrahydrofuran (15 mL), followed immediately by rapid syringe addition of a −78° C. solution of 3-(1,3-dioxolane ketal)-1-(3-cyclopentyloxy-4-methoxyphenyl)cyclobutane-1-carboxaldehyde (2.08 g, 6.25 mmol) (preparation described in patent) in tetrahydrofuran (15 mL). The reaction was stirred at room temperature for 1.5 h, was quenched with ammonium chloride and water and was extracted with three portions of dichloromethane. The organic extract was dried (magnesium sulfate) and evaporated. Purification by flash chromatography, eluting with 15:85 ethyl acetate: hexanes provided product as an off-white, waxy solid (1.39 g, 68%), m.p. 55–56° C.

1b 3-(3-Cyclopentyloxy-4-methoxyphenyl)-3-ethynylcyclobutan-1-one. A solution of 3-(3-cyclopentyloxy-4-methoxyphenyl)-3-ethynylcyclobutan-1-(1,3-dioxolane ketal) in tetrahydrofuran (65 mL) and 10% hydrochloric acid (15 mL) was stirred at 50–60° C. under an argon atmosphere for 24 h. The reaction was cooled, was poured into 5% sodium carbonate (100 mL) and was extracted with three portions of dichloromethane. The organic extract was dried (magnesium sulfate) and evaporated. Purification by flash chromatography, eluting with 1:9 ethyl acetate: hexanes provided product as a white solid (1.00 g, 83%), m.p. 58–59° C.

1c 3-(3-Cyclopentyloxy-4-methoxyphenyl)-3-phenylethynylcyclobutan-1-one. To a solution of 3-(3-cyclopentyloxy-4-methoxyphenyl)-3-ethynylcyclobutan-1-one (0.15 g, 0.53 mmol) in triethylamine (3 mL) was added iodobenzene (0.06 mL, 0.53 mmol), tetrakis(triphenylphosphine)palladium(0) (0.024 g, 4%) and copper (I) iodide (0.006 g, 6%). The reaction was stirred at 80–85° C. under an argon atmosphere for 1 h, was cooled, was diluted with water and was extracted with three portions of dichloromethane. The organic extract was dried (magnesium sulfate) and evaporated. Purification by flash chromatography, eluting with 1:9 ethyl acetate: hexanes provided product as a yellow oil (0.12 g, 60%).

Analysis Calcd for $C_{24}H_{24}O_3 \cdot 0.125 H_2O$: C 79.48, H 6.74; found: C 79.30, H 6.58.

Example 2 trans-1-Aminomethyl-3-(3-cyclopentyloxy-4-methoxyphenyl)-3-phenylethynylcyclobutane.

2a Methoxy 3-(3-cyclopentyloxy-4-methoxyphenyl)-3-phenylethynylcyclobut-1-ylidene. To a suspension of methoxymethyl)triphenylphosphonium chloride (0.94 g, 2.73 mmol) in diethyl ether (20 mL) at 0° C. under an argon atmosphere was rapidly added a solution of 1.8 M phenyllithium in cyclohexane/diethyl ether (4.95 mL, 8.9 mmol), followed immediately by a solution of 3-(3-cyclopentyloxy-4-methoxyphenyl)-3-phenylethynylcyclobutan-1-one (0.82 g, 2.28 mmol) (prepared in example 12b) in diethyl ether (20 mL). The reaction was stirred at room temperature for 24 h, was quenched with ammonium chloride, was diluted with water and was extracted with three portions of dichloromethane. The organic extract was dried (magnesium sulfate) and evaporated. Purification by flash chromatography, eluting with 1:9 ethyl acetate: hexanes provided product as a colorless oil (0.35 g, 40%). (Starting aldehyde was also recovered (0.36 g, 44%)).

2b trans-3-(3-Cyclopentyloxy-4-methoxyphenyl)-3-phenylethynylcyclobutan 1-carboxaldehyde and cis-3-(3-cyclopentyloxy-4-methoxyphenyl)-3-phenylethynylcyclobutan-1-carboxaldehyde. A solution of methoxy 3-(3-cyclopentyloxy-4-methoxyphenyl)-3-phenylethynylcyclobut-1-ylidene (0.45 g, 1.16 mmol) in isopropanol (5 mL) and water (5 mL) was deoxygenated, and then was treated with p-toluenesulfonic acid (0.02 g, 10%). The reaction was stirred at reflux under an argon atmosphere for 20 h, was cooled, was diluted with water and was extracted with three portions of dichloromethane. The organic extract was dried (magnesium sulfate) and evaporated. Purification by flash chromatography, eluting with 5:95 ethyl acetate : hexanes provided both products: trans-3-(3-Cyclopentyloxy-4-methoxyphenyl)-3-phenylethynylcyclobutan-1-carboxaldehyde was obtained as a colorless oil (0.11 g, 26%), Rf=0.23 (1:9 ethyl acetate: hexanes), and cis-3-(3-cyclopentyloxy-4-methoxyphenyl)-3-phenylethynylcyclobutan-1-carboxaldehyde was obtained as a colorless oil (0.15 g, 35%), Rf=0.16 (1:9 ethyl acetate: hexanes), contaminated with −10% trans isomer. Additional product (0.044 g, 10%) was isolated as a mixture of isomers.

2c trans-1-Aminomethyl-3-(3-cyclopentyloxy-4-methoxyphenyl)-3--phenylethynylcyclobutane. A mixture of trans-3-(3-cyclopentyloxy-4-methoxyphenyl)-3-phenylethynylcyclobutan-1-carboxaldehyde (0.11 g, 0.30 mmol), ammonium acetate (0.23 g, 3.0 mmol), sodium cyanoborohydride (0.019 g, 0.30 mmol) and several 4A molecular sieves in methanol (3 mL) was stirred at room temperature under an argon atmosphere for 3d. The reaction was treated with a crystal of methyl orange, then dropwise with hydrogen chloride-saturated methanol to attain a red color. The reaction was stirred for three hours, maintaining the acidity, was basified with 10% sodium hydroxide, was diluted with water and was extracted with three portions of 5/95 methanol/dichloromethane. The organic extract was dried (potassium carbonate) and evaporated. Purification by flash chromatography, eluted with 1:9 methanol: dichloromethane provided product as an amber oil (0.026 g, 23%). $^1$H-NMR (CDCl$_3$, 400 mHz) δ7.39 (m, 2H), 7.24 (m, 3H), 6.98 (d, J=2.3Hz, 1H), 6.91 (d, J=8.3 Hz, 1H), 6.79 (d, J=8.3 Hz, 1H), 4.78 (m, 1H), 3.80 (s, 3H), 3.13 (m, 1H), 3.05 (m, 2H), 2.82 (m, 2H), 2.36 (m, 2H), 1.8–2.0 (m, 6H), 1.65 (m, 2H) ppm. Mass spectrum (ES+): 376 (M+H).

Example 3 cis-1-Aminomethyl-3-(3-cyclopentyloxy-4-methoxyphenyl)-3-phenylethynylcyclobutane, A mixture of cis-3-(3-cyclopentyloxy-4-methoxyphenyl)-3-phenylethynylcyclobutan-1-carboxaldehyde (0.15 g, 0.41 mmol), ammonium acetate (0.31 g, 4.1 mmol), sodium cyanoborohydride (0.026 g, 0.41 mmol) and several 4A molecular sieves in methanol (3 mL) was stirred at room temperature under an argon atmosphere for 3d. The reaction was treated with a crystal of methyl orange, then dropwise with hydrogen chloride-saturated methanol to attain a red color. The reaction was stirred for three hours, maintaining the acidity, was basified with 10% sodium hydroxide, was diluted with water and was extracted with three portions of 5/95 methanol/dichloromethane. The organic extract was dried (potassium carbonate) and evaporated. Purification by flash chromatography, eluted with 5:95 methanol : dichloromethane provided product as an amber oil (0.029 g, 19%). $^1$H-NMR (CDCl$_3$, 400 MHz) δ7.39 (m, 2H), 7.25 (m, 3H), 7.09 (s, 1H), 7.04 (d, J=8.5 Hz, 1H), 6.81 (d, J=8.5Hz, 1H), 4.80 (m, 1H), 3.82 (s, 3H), 3.20 (m, 2H), 2.83 (m, 2H), 2.66 (m, 1H), 2.54 (m, 2H), 1.8–2.0 (m, 6H), 1.65 (m, 2H) ppm. Mass spectrum (ES+) 376 (M+H), 359 (M+H-NH$_3$), 291 (M+H-(O-cyclopentyl)). (The MS has numerous other peaks as well)

Example 4 trans-1-Amino-3-(3-cyclopentyloxy-4-methoxyphenyl)-3-phenylethynylcyclobutane, 4a 3-(3-Cyclopentyloxy-4-methoxyphenyl)-3-ethynylcyclobutan-1-ol. To a solution of 3-(3-cyclopentyloxy-4-methoxyphenyl)-3-ethynylcyclobutan-1-one (0.50 g, 1.76 mmol) (prepared in example 2b) in tetrahydrofuran (10 mL) at −30–40° C. under an argon atmosphere was added over 15 min a slurry of lithium borohydride (0.12 g, 5.28 mmol) in tetrahydrofuran (16 mL). The reaction was stirred 0.5 h and was poured into 0° C. ammonium chloride. 10% Hydrochloric acid was used to adjust to pH 3–4, the mixture was warmed to room temperature and was extracted with three portions of diethyl ether. The organic extract was dried (magnesium sulfate) and was evaporated. Purification by flash chromatography, eluting with 2:8 ethyl acetate : hexanes provided product as a colorless oil (0.54 g, 100%). $^1$H-NMR indicated the cis:trans isomer ratio to be ~85:15.

4b trans-3-(3-Cyclopentyloxy-4-methoxyphenyl)-3-ethynyl-1-phthalimidocyclobutane. A solution of 3-(3-cyclopentyloxy-4-methoxyphenyl)-3-ethynylcyclobutan-1-ol (0.54 g, 1.76 mmol) in tetrahydrofuran (20 mL) was treated with phthalimide (0.39 g, 2.64 mmol), triphenylphosphine (0.69 g, 2.64 mmol) and diethyl azodicarboxylate (0.42 mL, 2.64 mmol). The reaction was stirred at room temperature under an argon atmosphere for 24 h and was evporated. Purification by four flash chromatographies, eluting with 1:9 ethyl acetate: hexanes, with 5:48:48 ethyl acetate: dichloromethane: hexanes, with 4:24:72 ethyl acetate: dichloromethane: hexanes and with 2:20:80 ethyl acetate: dichloromethane: hexanes provided product as a white solid (0.57 g, 78%), m.p. 130–131° C. Some cis-3-(3-cyclopentyloxy4-methoxyphenyl)-3-ethynyl-1-phthalimidocyclobutane (0.08 g, 11%) was also isolated.

4c trans-1-tertbutoxycarbonylamino-3-(3-cyclopentyloxy-4-methoxyphenyl)-3-ethynylcyclobutane. A solution of trans-3-(3-cyclopentyloxy-4-methoxyphenyl)-3-ethynyl-1-phthalimidocyclobutane (0.24 g, 0.58 mmol) in ethanol (4 mL) and tetrahydrofuran (2 mL) was treated with hydrazine monohydrate (0.26 mL, 5.8 mmol) and was stirred at room temperature under an argon atmosphere for 18 h. The reaction was diluted with water and extracted with three portions of 5/95 methanol/dichloromethane. The organic extract was dried (magnesium sulfate) and evaporated to provide crude amine as a colorless oil. The crude intermediate was dissolved in dichloromethane (20 mL) and was treated with ditert.butyl dicarbonate (0.13 g, 0.61 mmol). The reaction was stirred at room temperature under an argon atmosphere for 24 h, was partitioned between dichloromethane and water, was dried (magnesium sulfate) and was evaporated. Purification by flash chromatography, eluting with 1:9 ethyl acetate :hexanes provided product as a whitish solid (0.098 g, 44%), m.p.129–130° C.

4d trans-1-tertbutoxycarbonylamino-3-(3-cyclopentyloxy-4-methoxyphenyl)-3-phenylethynylcyclobutane. A solution of trans-1-tertbutoxycarbonylamino-3-(3-cyclopentyloxy-4-methoxyphenyl)-3-ethynylcyclobutane (0.098 g, 0.25 mmol) in triethylamine (3 mL) was treated with iodobenzene (0.03 mL, 0.25 mmol), tetrakis(triphenylphosphine)palladium(0) (0.01 g, 4%) and copper(II) iodide (0.003 g, 6%). The reaction was stirred at 80–85° C. under an argon atmosphere for 1 h, was cooled, was diluted with water and was extracted with three portions of dichloromethane. The organic extract was dried (magnesium sulfate) and evaporated. Purification by flash chromatography, eluting with 1:9 ethyl acetate: hexanes provided product as a yellow solid (0.09 g, 78%), m.p.45–51° C.

4e trans-1-Amino-3-(3-cyclopentyloxy-4-methoxyphenyl)-3-phenylethynylcyclobutane. A solution of trans-1-tertbutoxycarbonylamino-3-(3-cyclopentyloxy-4-methoxyphenyl)-3-phenylethynylcyclobutane (0.09 g, 0.20 mmol) in dichloromethane (3 mL) was treated with trifluoroactic acid (0.15 mL, 2 mmol) and was stirred at room temperature under argon for 24 h. The reaction was again treated with trifluoroactic acid (0.15 mL, 2 mmol) and was stirred at room temperature under argon for 24 h, was cooled to 0° C., was quenched with sodium bicarbonate and water and was extracted with three portions of 5/95 methanol/dichloromethane. The organic extract was dried (potassium carbonate) and evaporated. Purification by two flash chromatographies, eluting first with 3:97 methanol: dichloromethane, then with 2:98 methanol: dichloromethane provided product as a yellow oil (0.039 g, 55%).

Analysis Calcd for $C_{24}H_{27}NO_2$·0.75 $H_2O$: C 76.87, H 7.66, N 3.74; found: C 77.13, H 7.48, N 3.95.

Example 5 trans-1-Amino-3-(2-aminopyrimidin-5-ylethynyl)-3-(3-cyclopentyloxy-4-methoxyphenyl)cyclobutane, 15a trans-3-(2-aminopyrimidin-5-ylethynyl)-1-tertbutoxycarbonylamino-3-(3-cyclopentyloxy-4-methoxyphenyl)cyclobutane. A solution of trans-1-tertbutoxycarbonylamino-3-(3-cyclopentyloxy-4-methoxyphenyl)-3-ethynylcyclobutane (0.098 g, 0.25 mmol) (prepared in example 4c) in dimethyl sulfoxide (1.5 mL) was added to a mixture of 2-amino-5-iodopyrimidine (0.07 g, 0.30 mmol), diethylamine (0.06 mL, 0.60 mmol) and a spatula-tip each of tetrakis(triphenylphosphine)palladium(0) and copper(II) iodide in dimethyl sulfoxide (1.5 mL). The reaction was stirred at 65–70° C. under an argon atmosphere for 4 h, was cooled, was diluted with ammonium chloride and water and was extracted with two portions of ethyl acetate. The organic extract was washed three times with water, once with brine, was dried (magnesium sulfate) and was evaporated. Purification by flash chromatography, eluting with 35:65 ethyl acetate: hexanes provided product as an off-white foam (0.10 g, 66%), m.p.63–67° C.

5b trans-1-Amino-3-(2-aminopyrimidin-5-ylethynyl)-3-(3-cyclopentyloxy-4-methoxyphenyI)cyclobutane. A solution of trans-3-(2-aminopyrimidin-5-ylethynyl)-1-tertbutoxycarbonylamino-3-(3-cyclopentyloxy-4-methoxyphenyl)cyclobutane (0.10 g, 0.20 mmol) in dichloromethane (5 mL) was treated with trifluoroactic acid (0.16 mL, 2 mmol) and was stirred at room temperature under argon for 9d. The reaction was quenched with sodium bicarbonate and water and was extracted with three portions of 5/95 methanol/dichloromethane. The organic extract was dried (magnesium sulfate) and evaporated. Purification by flash chromatography, eluting with 0.5:5:95 ammonium hydroxide: methanol: dichloromethane provided product as a pale tan solid (0.037 g, 48%), m.p.126–128° C.

Analysis Calcd for $C_{22}H_{26}N_4O_2 \cdot H_2O$: C 66.64, H 7.12, N 14.13; found: C 66.43, H 6.81, N 13.87.

Example 6 trans-1-Amino-3-(3-cyclopentyloxy-4-methoxyphenyl)-3-(3-nitrophenyl)ethynylcyclobutane, hydrochloride salt 6a trans-1-azido-3-(3-Cyclopentyloxy-4-methoxyphenyl)-3-ethynylcyclobutane. A solution of 3-(3-cyclopentyloxy-4-methoxyphenyl)-3-ethynylcyclobutan-1-ol (3.35 g, 11.7 mmol) (prepared in example 4a) in tetrahydrofuran (125 mL) at 0° C. under an argon atmosphere in a foil-wrapped flask was treated with triphenylphosphine (6.14 g, 23.4 mmol), then dropwise first with diethyl azodicarboxylate (3.7 mL, 23.4 mmol), then with diphenyl phosphorylazide (5.05 mL, 23.4 mmol). The reaction was stirred at room temperature under an argon atmosphere for 20 h and was evaporated. Purification by flash chromatography, eluting with 1:99 ethyl acetate: hexanes provided product as a colorless oil (1.62 g, 61%). Further chromatography allowed recovery of cis-1 -azido-3-(3-cyclopentyloxy-4-methoxyphenyl)- 3-ethynylcyclobutane (0.12 g, 3%), containing -10% trans isomer (by $^1$H-NMR).

6b trans-1-Azido-3-(3-cyclopentyloxy-4-methoxyphenyl)-3-(3-nitrophenyl)ethynylcyclobutane. A solution of trans-1-azido-3-(3-cyclopentyloxy-4-methoxyphenyl)-3-ethynylcyclobutane (0.20 g, 0.64 mmol) in triethylamine (5 mL) was treated with 3-nitro-iodobenzene (0.14 mL, 0.64 mmol), tetrakis(triphenylphosphine)palladium(0) (0.03 g, 4%) and copper (II) iodide (0.008 g, 6%). The reaction was stirred at 80–85° C. under an argon atmosphere for 0.5 h, was cooled, was diluted with water and was extracted with three portions of dichloromethane. The organic extract was dried (magnesium sulfate) and evaporated. Purification by flash chromatography, eluting with 1:9 ethyl acetate: hexanes provided product as a yellow oil (0.19 g, 69%).

6c trans-1-Amino-3-(3-cyclopentyloxy-4-methoxyphenyl)-3-(3-nitrophenyl)ethynylcyclobutane, hydrochloride salt. A solution of trans-1-azido-3-(3-cyclopentyloxy-4-methoxyphenyl)-3-(3-nitrophenyl) ethynylcyclobutane (0.19 g, 0.44 mmol) in 50% ammoniacal methanol (5 mL) and pyridine (5 mL) was treated with triphenylphosphine (0.35 g, 1.32 mmol). The reaction was stirred for 24 h at room temperature under an argon atmosphere, was diluted with water and was extracted with 5/95 methanol/dichloromethane. The organic extract was dried (magnesium sulfate) and evaporated. Purification by flash chromatography, eluting with 2:98 methanol : dichloromethane, followed by treatment of the free amine with hydrogen chloride-diethyl ether provided product as a tan solid (0.11 g, 59%), m.p.113–117° C.

Analysis Calcd for $C_{24}H_{26}N_2O_4 \cdot HCl \cdot 0.75 H_2O$: C 63.15, H 6.29, N 6.14; found: C 63.14, H 5.90, N 5.92

Proceeding in a similar manner, the following compounds were made.

trans-1-Amino-3-(3-cyclopentyloxy-4-methoxyphenyl)-3-(4-nitrophenyl)ethynylcyclobutane, hydrochloride salt, : m.p.162–163° C. Analysis Calcd for $C_{24}H_{26}N_2O_4 \cdot HCl \cdot H_2O$: C 62.54, H 6.34, N 6.07; found: C 62.56, H 5.94, N 5.

trans-1-Amino-3-(3-cgclopentyloxy-4-methoxyphenyl)-3-(4-trifluoromethoxyphenyl)ethynylcyclobutane, hydrochloride, SB 259835 A salt: m.p.170–174° C. Analysis Calcd for $C_{25}H_{26}F_3NO_3 \cdot HCl \cdot 0.65 H_2O$: C 60.83, H 5.78, N 2.84; found: C 60.87, H 5.58, N 2.86.

cis-1 -Amino-3-(3-cyclopentyloxy-4-methoxyphenyl)-3-phenylethynylcyclobutane, hydrochloride salt. SB259717 A: m.p.131–132° C. Analysis Calcd for $C_{24}H_{27}NO_2 \cdot HCl \cdot 1.75 H_2O$: C 67.12, H 6.57, N 3.26; found: C 67.05, H 6.20, N 3.15.

Example 7 trans-1-Amino-3-[(3-carboxyphenyl)ethynyl]3-(3-cyclopentyloxy-4-methoxyphenyl)cyclobutane, hydrochloride salt 7a trans-1-Amino-3-[(3-carboxymethylphenyl)ethynyl]3-(3-cyclopentyloxy-4-methoxyphenyl)cyclobutane. This product was prepared as the free amine, but otherwise in a manner similar to trans-1-amino-3-(3-cyclopentyloxy-4-methoxyphenyl)-3-(3-nitrophenyl)ethynylcyclobutane, hydrochloride salt. m.p.70–72° C.

7b trans-1-Amino-3-[(3-carboxyphenyl)ethynyl] 3-(3-cyclopentyloxy-4-methoxyphenyl)cyclobutane, hydrochloride salt. A solution of trans-1-amino-3-[(3-carboxymethylphenyl)ethynyl]3-(3-cyclopentyloxy-4-methoxyphenyl)cyclobutane (0.28 g, 0.68 mmol) and potassium hydroxide (0.12 g, 2.03 mmol) in tetrahydrofuran (5 mL), methanol (5 mL) and water (2 mL) was stirred at room temperature under an argon atmosphere for 24 h. The reaction was acidified with ethereal hydrogen chloride and evaporated. Purification by reverse-phase flash chromatography, eluting with 6:4 methanol : water provided free amine as a white solid (0.19 g, 71%), m.p.177–180° C. The free amine was suspended in dichloromethane, was treated with ethereal hydrogen chloride, was filtered and was died. Resuspension in methanol, filtration, evaporation and drying provided product as a white solid (0.09 g, 29%), m.p. greater than 225° C. Analysis Calcd for $C_{25}H_{27}NO_4 \cdot HCl \cdot 3 H_2O$: C 60.54, H 5.69, N 2.82; found: C 60.38, H 5.74, N 2.69.

Proceeding in a similar manner, the following compound was made:

trans-1-Amino-3-[(4-carboxyphenyl)ethynyl]3-(3-cyclopentyloxy-4-methoxyphenyl)cyclobutane, hydrochloride salt, :m.p.greater than 225° C. Analysis Calcd for $C_{25}H_{27}NO_4 \cdot HCl \cdot 1.5 H_2O$: C 64.03, H 6.66, N 2.99; found: C 64.22, H 6.26, N 2.78.

UTILITY EXAMPLES

Example A

Inhibitory effect of compounds of Formula (I) and (II) on in vitro TNF production by human monocytes The inhibitory effect of compounds of Formula (I) and (II) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I) and (II). The protocol used in these models is described in Badger et al., EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

Example C

Isolation of PDE Isozymes

The phosphodiesterase inhibitory activity and selectivity of the compounds of Formula (I) and (II) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE 4, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE 4 is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive IC50's in the nanomolar to μM range for compounds of the workings examples described herein for Formula (I) and (II) have been demonstrated.

What is claimed is:

1. A compound of Formula (I)

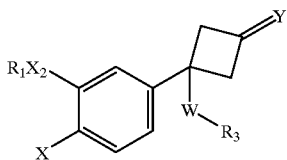

(I)

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be unsubstituted or substituted with one or more fluorines;

m is 0 to 2;

n is 1 to 4;

r is 0 to 6;

$R_4$ and $R_5$ are independently hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in —$(CR_4R_5)_nO(CR_4R_5)_mR_6$;

X is $VR_2$, halogen, nitro, $NR_4R_5$, or formyl amine;

V is O or $S(O)_{m'}$;

m' is 0, 1, or 2;

$X_2$ is O or $NR_8$;

$R_2$ is —$CH_3$ or —$CH_2CH_3$ unsubstituted or substituted by 1 or more fluorines;

$R_3$ is $COOR_{14}$, $C(O)NR_4R_{14}$ or $R_7$;

W is alkyl of 2 to 6 carbon atoms, alkenyl of 2 to 6 carbon atoms or alkynyl of 2 to 6 carbon atoms;

Z is O, $NR_9$, $NOR_8$, NCN, C(—CN)$_2$, $CR_8CN$, $CR_8NO_2$, $CR_8C(O)OR_8$, $CR_8C(O)NR_8R_8$, C(—CN)$NO_2$, C(—CN)$C(O)OR_9$, C(—CN)$C(O)NR_8R_8$;

Y is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$, or =Y is 2-(1,3-dithiane), 2-(1,3-dithiolane), dimethylthio ketal, diethylthio ketal, 2-(1,3-dioxolane), 2(1,3-dioxane), 2-(1,3-oxathiolane), dimethyl ketal or diethyl ketal;

$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —C(O)$R_8$, —$CO_2R_8$, —O(CH$_2)_qR_8$, —CN, —C(O)$NR_{10}R_{11}$, —O(CH$_2)_qC(O)NR_{10}R_{11}$, —O(CH$_2)_qC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, or $R_{13}$;

q is 0, 1, or 2;

$R_{12}$ is $R_{13}$, $C_3$–$C_7$ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;

$R_8$ is hydrogen or $R_9$;

$R_{8'}$ is $R_8$ or fluorine;

$R_9$ is $C_{1-4}$ alkyl unsubstituted or substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_8$ and $R_{14}$ are as $NR_8R_{14}$ they may together with the nitrogen form a 5 to 7 membered ring comprised only of carbon atoms or carbon atoms and at least one heteroatom selected from O, N, or S; provided that:

$R_{15}$ is $C(O)R_{14}$, $C(O)NR_4R_{14}$, $S(O)_2R_7$, or $S(O)_2NR_4R_{14}$;

or a pharmaceutically acceptable salt thereof.

2. A compound of claim 1 wherein $R_1$ is —$CH_2$-cyclopropyl, cyclopentyl, 3-hydroxycyclopentyl, methyl or CF$_2$H; X is VR$_2$; V is oxygen; X$_2$ is oxygen; R$_2$ is CF$_2$H or methyl, W is ethynyl or 1,3-butadiynyl, R$_3$ is a substituted or unsubstituted phenyl or pyrimidinyl ring, and Z is O or NR$_7$.

3. A compound of claim 2 which is
3-(3-cyclopentyloxy-4-methoxyphenyl)-3-phenylethynylcyclobutan-1-one.

4. A compound of Formula (II)

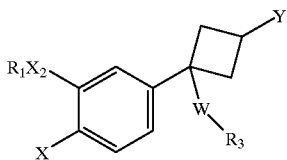

(II)

wherein:

R$_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties may be unsubstituted or substituted with one or more fluorines;

m is 0 to 2;

n is 1 to 4;

r is 0 to 6;

R$_4$ and R$_5$ are independently hydrogen or C$_{1-2}$ alkyl;

R$_6$ is hydrogen, methyl, hydroxyl, aryl, halo substituted aryl, aryloxyC$_{1-3}$ alkyl, halo substituted aryloxyC$_{1-3}$ alkyl, indanyl, indenyl, C$_{7-11}$ polycycloalkyl, tetrahydrofuranyl, furanyl, tetrahydropyranyl, pyranyl, tetrahydrothienyl, thienyl, tetrahydrothiopyranyl, thiopyranyl, C$_{3-6}$ cycloalkyl, or a C$_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;

provided that:

a) when R$_6$ is hydroxyl, then m is 2; or
b) when R$_6$ is hydroxyl, then r is 2 to 6; or
c) when R$_6$ is 2-tetrahydropyranyl, 2-tetrahydrothiopyranyl, 2-tetrahydrofuranyl, or 2-tetrahydrothienyl, then m is 1 or 2; or
d) when R$_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then R$_6$ is other than H in —(CR$_4$R$_5$)$_n$O(CR$_4$R$_5$)$_m$R$_6$;

X is VR$_2$, halogen, nitro, NR$_4$R$_5$, or formyl amine;

V is O or S(O)$_{m'}$;

m' is 0, 1, or 2;

X$_2$ is O or NR$_8$;

R$_2$ is —CH$_3$ or —CH$_2$CH$_3$ unsubstituted or substituted by 1 or more fluorines;

R$_3$ is COOR$_{14}$, C(O)NR$_4$R$_{14}$ or R$_7$;

W is alkyl of 2 to 6 carbon atoms, alkenyl of 2 to 6 carbon atoms or alkynyl of 2 to 6 carbon atoms;

Y is —(CR$_4$R$_5$)$_q$Z';

Y' is O or S;

Z' is OR$_{14}$, OR$_{15}$, SR$_{14}$, S(O)$_m$R$_7$, S(O)$_2$NR$_{10}$R$_{14}$, NR$_{10}$R$_{14}$, NR$_{14}$C(O)R$_9$, NR$_{10}$C(Y')R$_{14}$, NR$_{10}$C(O)OR$_7$, NR$_{10}$C(Y')NR$_{10}$R$_{14}$, NR$_{10}$S(O)$_2$NR$_{10}$R$_{14}$, NR$_{10}$C(NCN)NR$_{10}$R$_{14}$, NR$_{10}$S(O)$_2$R$_7$, NR$_{10}$C(CR$_4$NO$_2$)NR$_{10}$R$_{14}$, NR$_{10}$C(NCN)SR$_9$, NR$_{10}$C(CR$_4$NO$_2$)SR$_9$, NR$_{10}$C(NR$_{10}$)NR$_{10}$R$_{14}$, NR$_1$OC(O)C(O)NR$_{10}$R$_{14}$, or NR$_{10}$C(O)C(O)OR$_{14}$;

R$_7$ is —(CR$_4$R$_5$)$_q$R$_{12}$ or C$_{1-6}$ alkyl wherein the R$_{12}$ or C$_{1-6}$ alkyl group is unsubstituted or substituted one or more times by methyl or ethyl unsubstituted or substituted by 1–3 fluorines, —F, —Br, —Cl, —NO$_2$, —NR$_{10}$R$_{11}$, —C(O)R$_8$, —CO$_2$R$_8$, —O(CH$_2$)$_q$R$_8$, —CN, —C(O)NR$_{10}$R$_{11}$, —O(CH$_2$)$_q$C(O)NR$_{10}$R$_{11}$, —O(CH$_2$)$_q$C(O)R$_8$, —NR$_{10}$C(O)NR$_{10}$R$_{11}$, —NR$_{10}$C(O)R$_{11}$, —NR$_{10}$C(O)OR$_9$, —NR$_{10}$C(O)R$_{13}$, —C(NR$_{10}$)NR$_{10}$R$_{11}$, —C(NCN)NR$_{10}$R$_{11}$, —C(NCN)SR$_9$, —NR$_{10}$C(NCN)SR$_9$, —NR$_{10}$C(NCN)NR$_{10}$R$_{11}$, —NR$_{10}$S(O)$_2$R$_9$, —S(O)$_m$'R$_9$, —NR$_{10}$C(O)C(O)NR$_{10}$R$_{11}$, —NR$_{10}$C(O)C(O)R$_{10}$, or R$_{13}$;

q is 0, 1, or 2;

R$_{12}$ is R$_{13}$, C$_3$–C$_7$ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;

R$_8$ is hydrogen or R$_9$;

R$_{8'}$ is R$_8$ or fluorine;

R$_9$ is C$_{14}$ alkyl unsubstituted or substituted by one to three fluorines;

R$_{10}$ is OR$_8$ or R$_{11}$;

R$_{11}$ is hydrogen, or C$_{1-4}$ alkyl unsubstituted or substituted by one to three fluorines; or when R$_{10}$ and R$_{11}$ are as NR$_{10}$R$_{11}$ they may together with the nitrogen form a 5 to 7 membered ring comprised only of carbon atoms or carbon atoms and at least one heteroatom selected from O, N, or S;

R$_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C$_{1-2}$ alkyl groups;

R$_{14}$ is hydrogen or R$_7$; or when R$_8$ and R$_{14}$ are as NR$_8$R$_{14}$ they may together with the nitrogen form a 5 to 7 membered ring comprised only of carbon atoms or carbon atoms and at least one heteroatom selected from O, N, or S; provided that:

R$_{15}$ is C(O)R$_{14}$, C(O)NR$_4$R$_{14}$, S(O)$_2$R$_7$, or S(O)$_2$NR$_4$R$_{14}$;

or a pharmaceutically acceptable salt thereof.

5. A compound according to claim 4 wherein R$_1$ is —CH$_2$-cyclopropyl, cyclopentyl, 3-hydroxycyclopentyl, methyl or CF$_2$H; X is VR$_2$; V is oxygen; X$_2$ is oxygen; R$_2$ is CF$_2$H or methyl, W is ethynyl or 1,3-butadiynyl, R$_3$ is a substituted or unsubstituted phenyl or pyrimidinyl ring, and Z is OR$_{14}$, OR$_{15}$ or NR$_{10}$R$_{14}$.

6. A compound according to claim 5 which is:
trans-1-aminomethyl-3-(3-cyclopentyloxy-4-methoxyphenyl)-3-phenylethynylcyclobutane,
trans-1-amino-3-(3-cyclopentyloxy-4-methoxyphenyl)-3-phenylethynylcyclobutane,
trans-1-amino-3-(2-aminopyrimidin-5-ylethynyl)-3-(3-cyclopentyloxy-4-methoxyphenyl)cyclobutane,
trans-1-amino-3-(3-cyclopentyloxy-4-methoxyphenyl)-3-(3-nitrophenyl)ethynylcyclobutane, hydrochloride salt
trans-1-amino-3-(3-cyclopentyloxy-4-methoxyphenyl)-3-(4-nitrophenyl)ethynylcyclobutane, hydrochloride salt,
trans-1-amino-3-[(3-carboxyphenyl)ethynyl]3-(3-cyclopentyloxy-4-methoxyphenyl)cyclobutane, hydrochloride salt.

7. A pharmaceutical composition comprising a pharmaceutically acceptable excipient and a compound of Formula (I) according to claim 1.

8. A pharmaceutical composition comprising a pharmaceutically acceptable excipient and a compound of Formula (I) according to claim 4.

9. A method for treating asthma or chronic obstructive pulmonary disease comprising administering a compound of Formula (I) according to claim 1 in an amount sufficient to treat asthma or chronic obstructive pulmonary disease in a human.

10. A method for treating as asthma or chronic obstructive pulmonary disease comprising administering a compound of Formula (II) according to claim 4 in an amount sufficient to treat asthma or chronic obstructive pulmonary disease in a human.

\* \* \* \* \*